US009301707B2

(12) United States Patent
Dahan et al.

(10) Patent No.: US 9,301,707 B2
(45) Date of Patent: Apr. 5, 2016

(54) MR IMAGING IN SEPARATE ROOMS USING A MAGNET HAVING A DIAGNOSTIC TABLE

(71) Applicant: IMRIS INC., Winnipeg (CA)

(72) Inventors: Meir Dahan, Winnipeg (CA); Mark Alexiuk, Winnipeg (CA); Wayne Schellekens, Winnipeg (CA); Vlajko Srzic, Winnipeg (CA)

(73) Assignee: Imris Inc, Winnipeg, MB (CA)

( * ) Notice: Subject to any disclaimer, the term of this patent is extended or adjusted under 35 U.S.C. 154(b) by 349 days.

(21) Appl. No.: 13/670,944

(22) Filed: Nov. 7, 2012

(65) Prior Publication Data
US 2014/0128724 A1    May 8, 2014

(51) Int. Cl.
| | |
|---|---|
| A61B 5/05 | (2006.01) |
| A61B 5/055 | (2006.01) |
| A61B 5/00 | (2006.01) |
| G01R 33/38 | (2006.01) |
| A61G 13/02 | (2006.01) |
| A61G 13/00 | (2006.01) |
| A61G 12/00 | (2006.01) |

(52) U.S. Cl.
CPC ............. *A61B 5/0555* (2013.01); *A61B 5/0046* (2013.01); *A61B 5/6889* (2013.01); *A61B 5/704* (2013.01); *A61G 13/02* (2013.01); *G01R 33/3802* (2013.01); *A61G 12/004* (2013.01); *A61G 13/0018* (2013.01); *A61G 2210/50* (2013.01)

(58) Field of Classification Search
CPC .... A61B 5/0555; A61B 5/6889; A61B 5/704; A61B 5/0046; A61G 13/02; A61G 13/0018
See application file for complete search history.

(56) References Cited

U.S. PATENT DOCUMENTS

| | | | |
|---|---|---|---|
| 5,551,430 | A | 9/1996 | Blakeley et al. |
| 5,735,278 | A | 4/1998 | Hoult et al. |
| 8,295,905 | B2 | 10/2012 | Graves et al. |
| 2006/0260050 | A1 | 11/2006 | Manzione |
| 2007/0033889 | A1 | 2/2007 | Manzione |
| 2008/0039712 | A1 | 2/2008 | Graves et al. |
| 2009/0124884 | A1 | 5/2009 | Saunders et al. |
| 2010/0031443 | A1* | 2/2010 | Georgiev et al. ................. 5/601 |
| 2012/0256626 | A1* | 10/2012 | Adalsteinsson et al. ...... 324/309 |

OTHER PUBLICATIONS

IMRIS; "Visius Surgical Theatre" Issued Dec. 2011; pp. 0-7;www.imris.com.

(Continued)

*Primary Examiner* — Amanda Lauritzen Moher
*Assistant Examiner* — Joseph M Santos Rodriguez
(74) *Attorney, Agent, or Firm* — Adrian D. Battison; Ade & Company Inc.

(57) ABSTRACT

In MR imaging in a suite of rooms including a diagnostic room and a second surgical room, the magnet includes a diagnostic table separable from a docking station of the magnet and the second room includes a second surgical table. An imaging control computer controls operation of the imaging system and a movement control computer controls operation of the magnet moving system and the patient support table. During imaging in the surgical room, the diagnostic table is separated and docked at a secondary docking station while an emulating computer system cooperate with the imaging control computer system by emulating outputs from the disconnected diagnostic table for controlling operation of the imaging system.

11 Claims, 3 Drawing Sheets

(56) References Cited

OTHER PUBLICATIONS

"IMRISneuro 70 cm Bore 3T in Intra-Operative Neurosurgery"; Clinical Neurology; by Jeanne Elliott; Magnetom Flash 312009; pp. 74-79 Mar. 2009.

AANA Journal Course; Feb. 2000vol. 79, No. 1; Intraoperative Magnetic Resonance Imaging for Neurosurgical Procedures: Anesthetic Implications; pp. 71-77; by Bernadette Henrichs.

"Magnetom Area Transforming 1.5T Economics"; Siemens; pp. 1-22; Order No. A91MR-9011.10C-7600; 2012.

* cited by examiner

MR IMAGING IN SEPARATE ROOMS USING A MAGNET HAVING A DIAGNOSTIC TABLE

This invention relates to MR imaging in separate rooms using a magnet having a diagnostic table, where in a second room the diagnostic table is removed, for cooperation of the magnet with a separate table designed and dedicated to a particular intervention such as surgical procedures.

BACKGROUND OF THE INVENTION

In U.S. Pat. No. 5,735,278 (Houllt et al) issued Apr. 7, 1998, is disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients.

In U.S. Pat. No. 8,295,905 (Graves et al) issued Oct. 23, 2012 and originally published as 2008/0039712 on Feb. 14, 2008 is disclosed an improvement to the above arrangement where the magnet can rotate about a vertical axis to allow the magnet to be used in adjacent rooms where a diagnostic table associated with the magnet is used in one room and the magnet is used in another room for other intervention where a different table contained within the room is used.

It is well known that the diagnostic table provided for diagnostic MR imaging of patients and typically carried on or with the magnet is unsuitable for other interventions including surgical procedures and radiation treatments.

The arrangement of magnet and diagnostic table manufactured by Siemens under the trade mark Symphony (at a field strength of 1.5 Tesla or 1.5 T) Espree (1.5 T), Verio (3 T) for which the above Hoult and Graves proposal was designed carried a diagnostic table permanently attached to one end. In order to use the same magnet with the diagnostic table at one end it was necessary to rotate the magnet in or for the second room to allow the opposite end of the magnet to be used with the table contained within that room.

In recent years Siemens have introduced a new magnet system under the trade mark Aera (1.5 T) or Skyra (3 T) which is designed to image when the patient is supported by a dockable trolley-like table. The Siemens magnet is arranged to remain at a fixed location for use only with the dockable table and the table can be released from the magnet and moved to a separate location for preparation of the patient for imaging at a location away from the magnet. The trolley-like table is then moved up to the magnet where it docks with a fixed floor mounted docking head for mechanical and electrical connection between the magnet and the table. Once docked, imaging is carried out under control of the imaging computer where signals to and from the table are communicated through the docking head.

When the dockable table is not connected to the system, the scanner will not acquire an MR image (measurement). In this situation, imaging is disabled by design as the clinical workflows considered for scanner use were limited to diagnostic imaging and require a diagnostic-style table connected to the system. The scanner control system detects the absence of a docked table by means of a failure to establish and maintain a defined communications protocol with table components (actuators, sensors, communication buses). When the dockable table is connected, the communication protocol conveys information about different sensor and actuator states. The scanner control system can infer patient position in the scanner bore from these values and system settings such as patient registration (patient age, weight, height, orientation in scanner).

One value that is communicated using the protocol is the position of the patient table within the bore of the MRI scanner. This value, as well as others such as "table in desired position", is required for safe and effective operation of the scanner. For example, the scanner control system ensures safety of the patient with respect to RF energy absorbed by the patient by calculating and controlling a specific-absorption rate (SAR) setting. The SAR setting is based on many parameters including the patient height, weight, the anatomy to be imaged and the position of the patient table in the bore.

Use of the MRI scanner in a surgical setting, namely an operating room, requires that a surgical table be used to obtain the desired patient positioning for the procedure. The above named dockable tables are not suitable for surgical use due to limited forward/lateral tilt and the lack of mounting points for surgical equipment such as head fixation devices (HFD).

When the above magnet is used in an arrangement of the above Hoult or Graves type installation, the magnet is mounted on ceiling rails and is able to move from one imaging room to an adjacent imaging room. The second table in the second room supports the patient in a combined surgical-imaging position and provides mounting points for surgical equipment.

It is not possible therefore to use the Aera/Skyra (trade mark) magnet of Siemens with the above system of Hoult or Graves since the control system will not allow imaging without the dockable table being properly docked.

SUMMARY OF THE INVENTION

It is one object of the invention to provide a method for using a magnet having a diagnostic table, where in a second room the diagnostic table is removed, for cooperation of the magnet with a separate table designed and dedicated to a particular intervention such as surgical procedures.

According to one aspect of the invention there is provided a method method for imaging a part of each of a plurality of patients comprising:

providing a plurality of rooms each arranged for use in imaging a patient from said plurality of patients independently, the plurality of the rooms including at least a first room for a diagnostic procedure and a second room for an interventional procedure;

providing a magnetic resonance imaging system for obtaining images of a part of a patient of the plurality of patients, the magnetic resonance imaging system comprising:

a magnet having a cylindrical bore with a horizontal axis of the bore longitudinal of the magnet;

a field control arrangement for controlling and varying magnetic fields of the magnet, a radio frequency transmission and detection system for eliciting and detecting NMR signals from the part in response to the magnetic fields, an RF probe arranged to be located adjacent to the part at an imaging location in the bore, a display monitor for displaying the detected signals;

a diagnostic table arranged to be mounted at a first end of the bore for movement relative to the magnet longitudinally of the bore toward a second end of the bore for carrying the part of the patient into an imaging location in the bore, the diagnostic table being separable from the magnet so as to disconnected therefrom;

and an imaging control computer system for controlling operation of the imaging system including the field control arrangement, the detection system, the RF probe, the display monitor and the diagnostic table;

in the first room using the control computer system to effect imaging of a first patient of the plurality of patients using the magnetic resonance imaging system with the first patient located on the diagnostic table;

providing a magnet moving system for moving the magnet from the first room to the second room;

providing a patient support table mounted in the second room arranged for the interventional procedure on a second patient from said plurality of patients;

the patient support table being operable for movement of a patient support portion to different positions of the patient relative to the magnet;

the patient support table being arranged for cooperation with associated elements arranged for use in the interventional procedure;

providing a movement control computer system for controlling operation of the magnet moving system and the patient support table;

moving the magnet from the first room to the second room by:
  disconnecting the diagnostic table from the magnet so that the diagnostic table remains with the first room; and
  operating the movement control computer system to control operation of the magnet moving system and the patient support table;

so that in the second room the magnet and its bore is moved into a position surrounding the patient support table with the part of the second patient on the patient support table at the imaging location;

in the second room using the control computer system to effect imaging of a second patient of the plurality of patients using the magnetic resonance imaging system with the second patient located on the patient support table table;

and generating signals from an emulating computer system which cooperate with the imaging control computer system by emulating outputs from the disconnected diagnostic table for controlling operation of the imaging system.

Preferably the emulating computer system is a sub-component of the movement control computer system. However it may be a separate system designed for communication with the movement control computer system.

Preferably the emulating computer system establishes and maintains communication to the imaging control computer system using a defined protocol, where the defined protocol is established for use with the imaging control computer system.

In one arrangement the emulating computer system provides to the imaging control computer system required sensor values and actuator states to emulate the diagnostic table. That is the emulating computer system can supply and control all required signals.

Preferably however the diagnostic table when non-functional in the first room is still connected to the imaging control computer system by a separate coupling when imaging in the second room. In this way it can act to provide some of the required sensor values and actuator states to emulate the diagnostic table and the emulating computer system is connected to the separate coupling. In this way the emulating computer system is a simpler system which functions in conjunction with the diagnostic table to provide only those signals which are not provided by the diagnostic table Preferably there is provided in the first room a first coupling component or docking station for physical and control connection to a cooperating coupling component on the diagnostic table when the diagnostic table is in communication with the magnet and a second coupling component or docking station for physical and control connection to the cooperating coupling component on the diagnostic table when the diagnostic table is separated from the magnet and the emulating computer system communicates with the second docking station to provide the required signals.

In one case the first docking station is physically carried on the magnet so that it moves with the magnet between the rooms and acts to cooperate with the coupling on the diagnostic table when in the first room.

Preferably there is provided in the second room a simulating coupling component arranged to simulate the cooperating coupling component on the diagnostic table for physical and control connection to the first docking station carried on the magnet and the emulating computer system communicates with the second coupling component.

Preferably the movement control computer system prevents the magnet from moving if the system detects that the first coupling component is connected to the cooperating coupling component on the diagnostic table, that is the necessary disconnection of the diagnostic table has not occurred.

Preferably the first coupling component and the cooperating coupling component provide connection of power, sense lines and optical fibers to enable communication between the diagnostic table and the magnet.

Preferably the movement control computer system prevents the magnet from moving beyond a certain range if the system detects that the RF probe is still connected to RF receptacles on the magnet.

In accordance with an important aspect, the emulating computer system provides a look-up-table to map physical values to virtual values for communication to the imaging control computer system to enable safe and effective imaging. That is the emulating computer system can supply a virtual value for the position of one or more system parameters which are sufficient for the imaging control computer system to compute and control imaging and safety aspects of the system.

In particular the emulating computer system is preferably arranged to provide a virtual value for the position of the patient table position which is sufficient for the imaging control computer system to compute and control specific-absorption rate (SAR).

In order to achieve this preferably both the emulating computer system and the imaging control computer system computer are provided with information on patient height/weight, age, position on the table, orientation to the magnet and the emulating computer system has a look up table (LUT) to convert magnet position along the patient support table to a value that the imaging control computer system expects to compute and control specific-absorption rate (SAR).

The invention provides therefore a hardware emulator that provides all necessary interfaces and information to enable imaging of the Siemens Aera/Skyra (trademark) MRI scanners in an operating room where the standard dockable table is not used.

The emulating computer system establishes and maintains communication to the imaging control computer system using the defined protocol; it provides appropriate sensor values and actuator states; it ensures that all information is provided for the original control system to compute and put into effect all safety measures such as SAR calculations; it enables safe and effective imaging of the Aera/Skyra MRI scanners in a non-standard configuration.

The emulating computer system is remotely located from the scanner e.g. located in the diagnostic room when the scanner is in the operating room.

The emulating computer system provides a novel use of a sub-system to enable an unforeseen use of the system.

The emulating computer system provides a virtual value to enable safe and effective operation of the MRI scanner system.

The emulating computer system provides a look-up-table to map physical values, that is, mobile magnet distance over the fixed table, to virtual values (e.g. patient table position into fixed magnet bore) to enable safe and effective imaging.

The preferred implementation is a two or three room configuration of imaging suites where the central room of three is a diagnostic imaging room.

The diagnostic rooms all use the dockable table for imaging as normally intended. A secondary fixed docking station is located in the diagnostic room. When imaging occurs in an adjacent operating room, the dockable table is detached from its primary docking station proximal to the scanner. The dockable table is parked and connected to the secondary fixed docking station in the diagnostic room. Cabling provides power and connects copper sense lines as well as optical fibers and enables communication between the table components and the magnet which is now located in a different room.

A micro-computer is connected to the magnet mover system and is aware of the magnet's position along the rail. Stored in the micro-computer memory is the specific configuration of the operating room, namely the type of table, its position relative to the rails, the type of table top and its length, etc. A user interface device is supplied to mover the magnet to imaging position over the table and also supplies a virtual value for the position of one or more system parameters, e.g. the patient table position, which are sufficient for the scanner control system to compute and control imaging and safety aspects of the system, e.g. SAR.

As a first alternate solution, a software based solution is also possible. The software would involve interacting with the control messaging that is sent by the MRI scanner system to the table. Some messages could be transmitted to the table without change, others could be ignored safely, others could be modified and acted on by the table etc. In some circumstances, a standard reply could be sent in response to a system control message. All responses by such a software emulator would be designed to ensure safe and effective operation of the system.

As a second alternate solution, is also possible that all the control and/or actuating parts of the diagnostic table can be assembled into a box that is bolted onto the magnet. These devices would be inter-connected as they would normally in a diagnostic table (the "guts" of the table) and would maintain contact to the MRI scanner system through a switch which is controlled by the patient support table and the diagnostic table.

Thus, when the magnet is in the first diagnostic room and the diagnostic table is attached, the switch is arranged such that the system communicates to the diagnostic table.

Thus, when the magnet is in the second operating room and the diagnostic table is not attached, the switch is arranged such that the system communicates to the table emulator or emulating computer system.

For imaging in the second room, the diagnostic table is connected to the "parked docking station" in the corner of another room. Cables provide communication and control between the magnet and the table. Cables also provide control from the movement control computer system to the parked docking station.

The magnet moves into the second room and partially over the patient. A laser is used to find the anatomical site on the patient to be imaged. This position is recorded in the system and the user pushes a button on a control pad which is "mark imaging position". The user is ready for imaging of the patient and pushes a second button which is "move to iso-centre". The magnet moves a fixed distance until the patient anatomy is in the iso-centre (middle of magnet).

The imaging control computer system has info on patient height/weight, age, position on the table (prone/supine), orientation to magnet (head first, feet first).

The movement control computer system has a look up table (LUT) to convert magnet position along the rail to a value that the imaging control computer system expects for correct system operation, namely diagnostic tabletop distance into the bore.

The emulating computer system uses the LUT to convert the distance along the rails to a corresponding diagnostic tabletop position and sends a control signal to the diagnostic table.

The diagnostic tabletop moves an appropriate distance. The imaging control computer system notes the table movement and sets its internal state for imaging of the patient with the same SAR levels etc as if the imaging were taking place in a diagnostic setting with the patient on the diagnostic table and not in an inter-operative setting with the patient on the patient support table.

There are alternate methods to achieve this that do not involve physical moving of the tabletop. It is possible that the table and the parked docking station would not be required.

Firstly the system can operate by intercepting all or some of the communications between the system and the diagnostic table and providing the appropriate responses in order to enable imaging.

Secondly the system can operate by removing the key devices and actuators/sensors from the diagnostic table, placing them in a box such that they can perform the same actions as they would normally in the diagnostic table. This type of emulating computer system would be powered on when the magnet is in the second room for imaging and the diagnostic table is not attached to any docking station.

The system provides safety and enabling systems for MR imaging that include the hardware emulator.

There is provided a docking station for connection to a mobile diagnostic table by a mounted bracket on the front of the magnet. A second parked docking station for the mobile diagnostic table is provided fixed to the floor for example in a remote location in a corner of the room. Control and communication interconnections are provided between the imaging control computer system and the movement control computer system. A look up table is part of the movement control computer system that converts magnet position along the rail and over the patient support table to "diagnostic tabletop position into the magnet".

This system enables use of the Siemens system in an intra-operative setting.

This novel use of the system will provide the same safety ratings, such as that related to specific absorption rate, SAR, for intra-operative use as it has for existing diagnostic uses. By meeting these safety ratings, imaging will take the same amount of time to produce the same quality of image. Failure to meet, in an intra-operative setting, the conditions that the system expects in a diagnostic settings, can mean: that the system cannot acquire images, that the system will not operate under the same safety constraints, that images may be acquired but that they will take longer to acquire and/or that the system will insert wait intervals between successive MR scans.

As part of the system, the emulating computer system is aware of which docking station has a table connected to it. There is a safety aspect in that the system interlocks will prevent the magnet mover system from moving if the system detects that the diagnostic table is connected to the docking station attached onto the magnet. Interlocks will also prevent rotation of the magnet if the diagnostic table is connected.

Further, interlocks will prevent motion of the magnet beyond a certain range if the system detects that the RF coils are still connected to the RF receptacles on the front of the MRI scanner.

Thus, when the magnet is in the first room and the diagnostic table is attached, the switch is arranged such that the system communicates to the diagnostic table. Thus, when the magnet is in the second room and the diagnostic table is not attached, the switch is arranged such that the system communicates to the emulating computer system.

The system can be used with a two room suite or other configurations are possible including a three room in line suite with two operating rooms flanking a center diagnostic room. In this case, for entry of the magnet into one of the operating rooms, rotation is not required.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
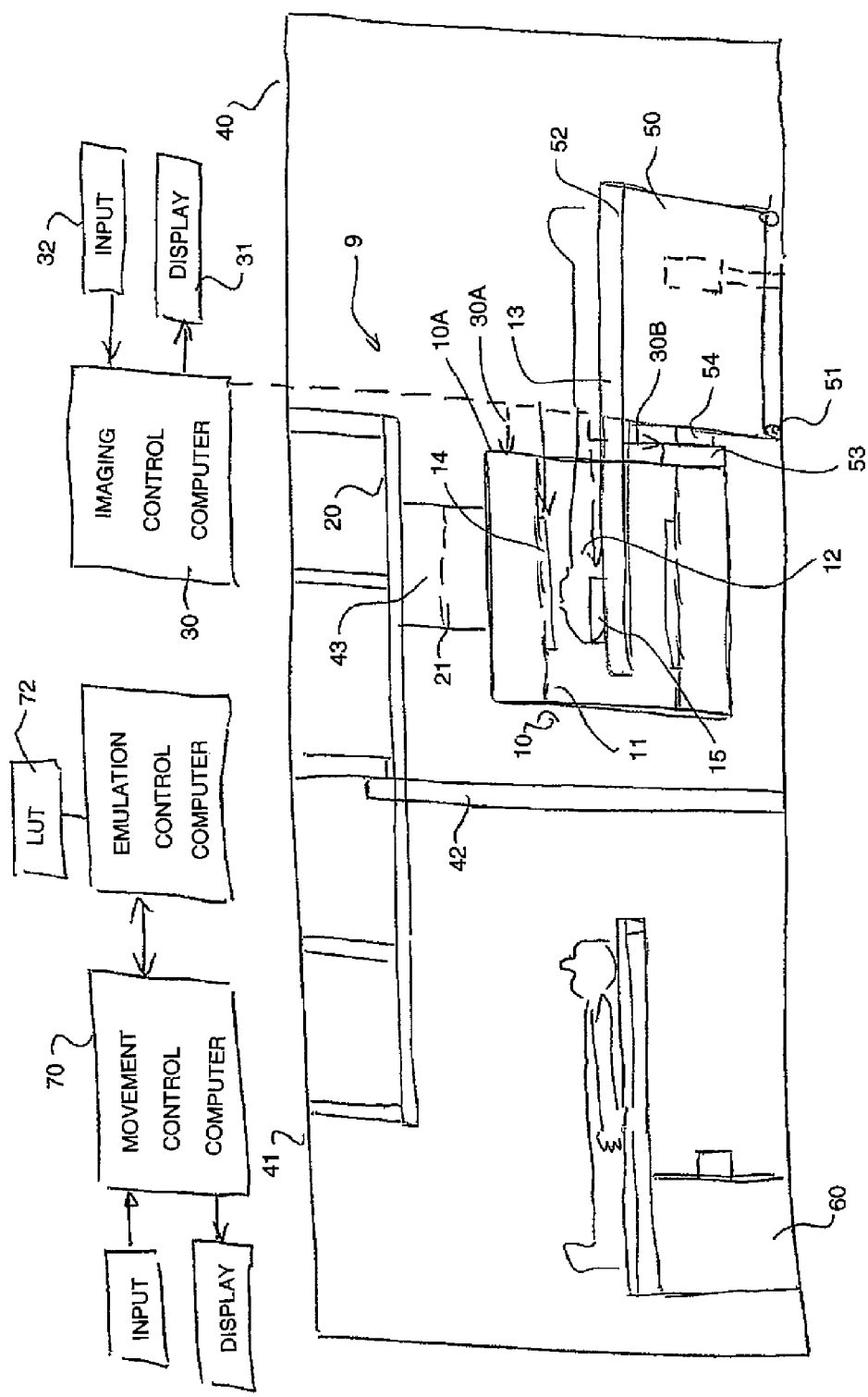
FIG. 1 is a first schematic side elevation of two rooms forming a suite for MR imaging where in the first room the magnet cooperates with the diagnostic table which attaches to locate the patient in place.

In FIG. 1 is shown schematically a magnetic resonance imaging system which includes a magnet 10 having a bore 11 into which a patient 12 can be received on a patient table 13. The system further includes an RF transmit body coil 14 which generates a RF field within the bore.

The movable magnet is carried on a rail system 20 with a support 21 suspended on the rail system. Further details of this construction as available from above U.S. Pat. No. 8,295,905 (Graves et al) assigned to the present assignees, the disclosure of which is incorporated herein by reference. This includes the rails 20 which carry the magnet from a first room 40 to a second room 41 through a door 42 and a magnet rotation mounting 43 which allows the magnet to rotate about a vertical axis at right angles to the bore 11 so that a front end 10A is presented toward the table in the room.

The system further includes a receive coil system generally indicated at 15 which is located at the isocenter within the bore and receives signals generated from the human body in conventional manner. An imaging control computer acts to control the magnet 10, the transmit body coil 14 and to receive the signals from the receive coil 15 for decoding the signal to generate images for display in a connected display system 31. The computer 30 is controlled by an operator using an operator input for the various parameters.

The method of the present invention is provided for imaging a part of each of a plurality of patients where the patients can be imaged in rooms 40 and 41 independently thus increasing the productivity of the imaging system. Thus the suite includes a plurality of at least two rooms 40 and 41 and possibly further rooms such as in a three room suite. Each room is arranged for use in imaging a patient from the plurality of patients independently. The first room 40 is arranged for a diagnostic procedure and the second room 41 is arranged for an interventional procedure, such as surgical procedures but also other interventions such as radiation treatment or the like.

For the suite of rooms is provided a magnetic resonance imaging system generally indicated at 9 for obtaining images of a part of a patient of the plurality of patients. The magnetic resonance imaging system includes the magnet 10 having the cylindrical bore 11 with a horizontal axis of the bore longitudinal of the magnet. The magnet includes a field control arrangement 30A operated by the control device 30 for controlling and varying magnetic fields of the magnet. The radio frequency transmission and detection system 14, 15 operates for eliciting and detecting NMR signals from the part in response to the magnetic fields. The RE probe 15 arranged to be located adjacent to the part at an imaging location at the ico-center in the bore. The detected signals are decoded and displayed on the display monitor 31.

A diagnostic table 50 is arranged to be mounted at a first end 10A of the bore 11 for movement relative to the magnet longitudinally of the bore 11 toward a second end of the bore for carrying the part of the patient 13 into the imaging location at the ico-center in the bore. The diagnostic table is of the type now manufactured and sold by Siemens under the above trademark which is separable from the magnet so as to disconnected therefrom and moved away on wheels 51. The table includes a table top 52 which can be moved over a limited range to locate the patient at the required position in the bore.

The imaging control computer system 30 acts for controlling operation of the imaging system including the field control arrangement, the detection system, the RF probe, the display monitor and the diagnostic table to effect the imaging process. Full details of a device of this type as manufactured by Siemens are well known to persons skilled in this art so that further detail is not required here.

In the first room 40, the control computer system is operated to effect imaging of a first patient of the plurality of patients using the magnetic resonance imaging system with the first patient located on the diagnostic table. The diagnostic table is operated to cooperate with the magnet by control signals which are supplied from the computer 30 to a docking station 53 of the magnet. The docking station cooperates with a cooperating coupling 54 on the table 50 to physically and electronically connect the docking station to the table. The docking station and the cooperating coupling component on the table provide connection of power, sense lines and optical fibers to enable communication between the diagnostic table and the magnet and particularly with the control computer 30 which controls both.

In order to carry out the imaging the computer 30 provides instructing signals to the various components and particularly to the table 50 and expects suitable responses to the instructing signals in the form of reply signals and sensor signals. The imaging can only proceed where the signals are properly communicated.

Figure 2:
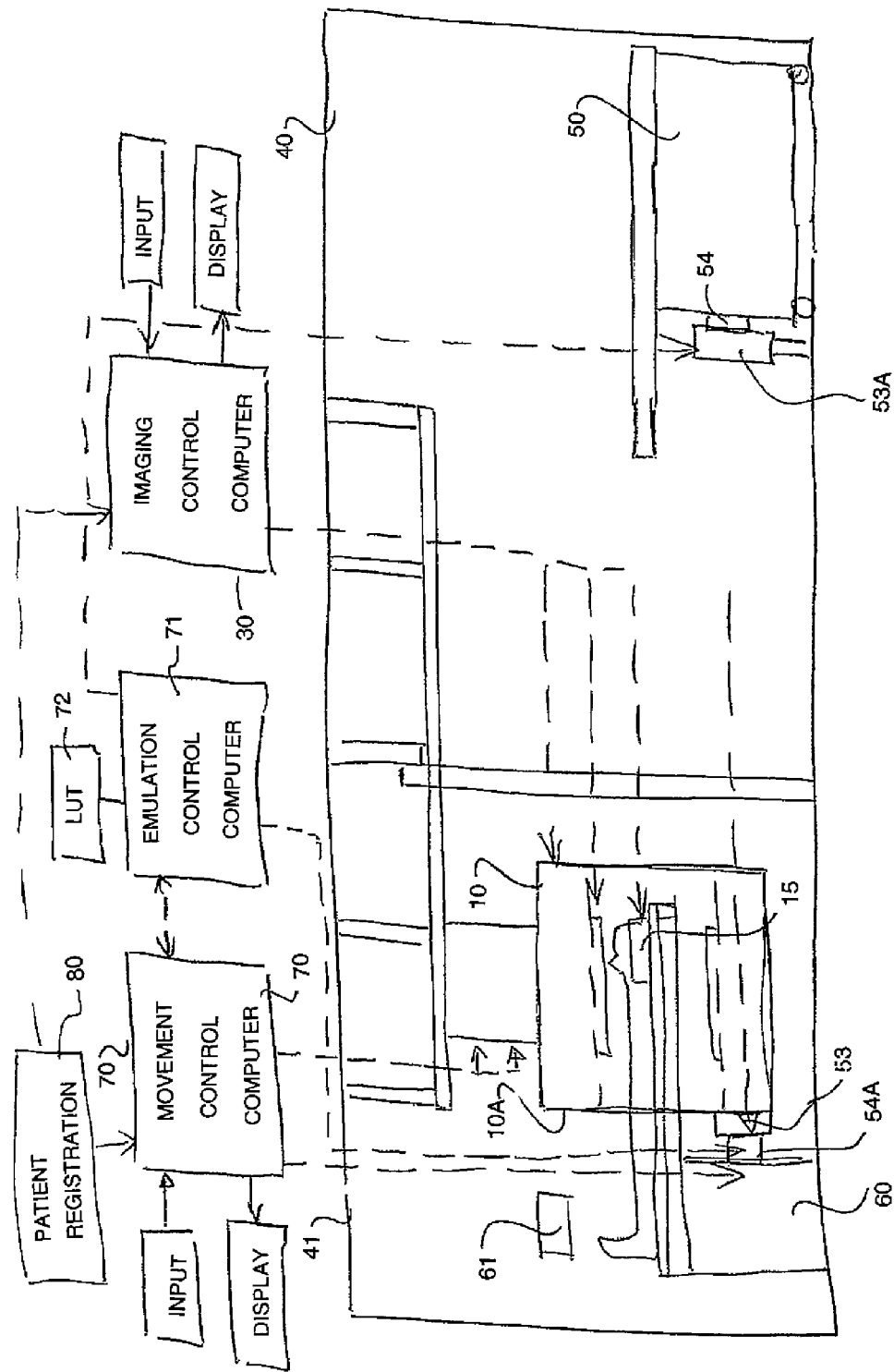
FIG. 2 is a second schematic side elevation of two rooms forming a suite for MR imaging where in the second room the magnet cooperates with a surgical table for surgical intervention on the patient.
Figure 3:
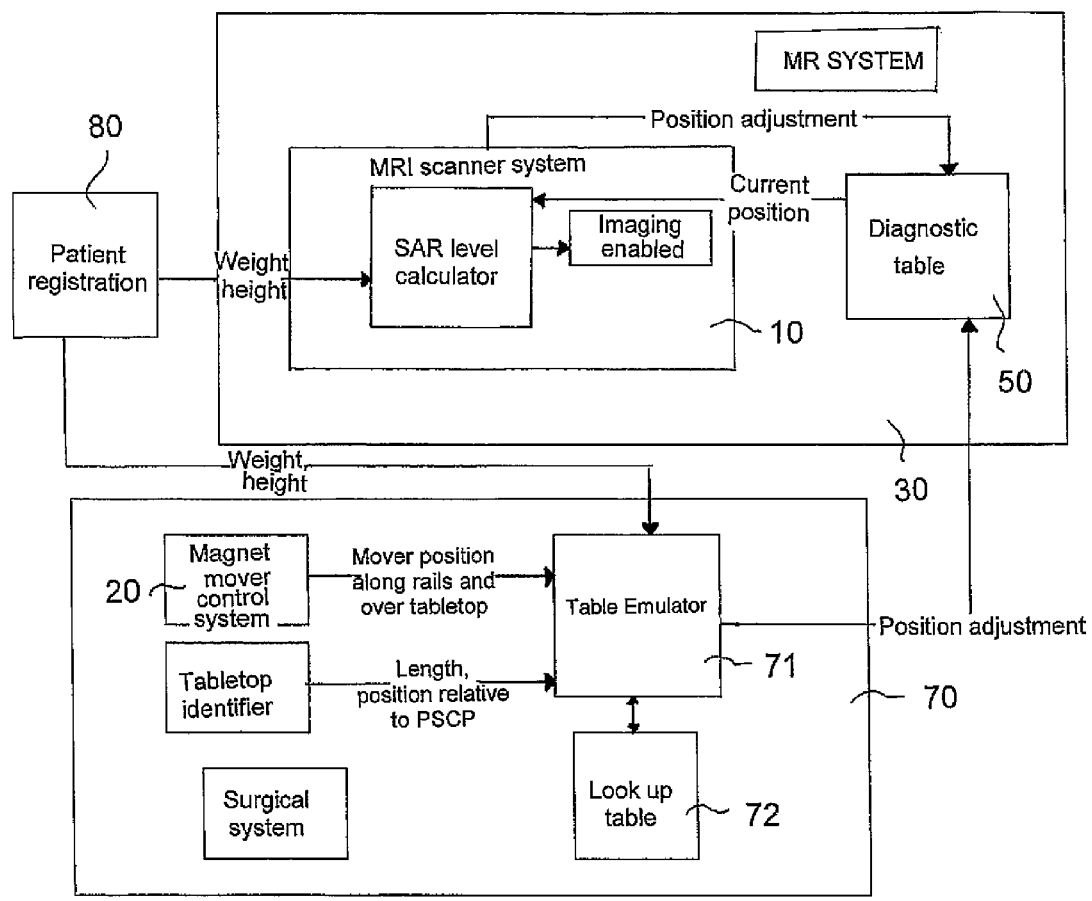
FIG. 3 is a schematic illustration of the control systems for the MR system and the Surgical system.

After the imaging in the first room is complete the magnet moving system operates for moving the magnet 10 from the first room 40 to the second room 41 as shown in FIG. 2. This movement includes linear movement along the rails and rotation about the vertical axis at the rotary coupling 43.

In the second room there is provided a patient support table 60 mounted and arranged for the interventional procedure on a second patient. The table is designed for the procedure so that it has characteristics not available at the table 50. These can include increased range of movement and connection to various accessories 61 required for the procedure. The patient support table 60 is operable for movement of a patient support portion to different positions of the patient relative to the magnet and is controlled by a dedicated movement control computer 70

The movement control computer system 70 acts to control operation of the magnet moving system and the patient support table so as to move the magnet from the first room to the second room by disconnecting the diagnostic table from the magnet so that the diagnostic table remains with the first room and controlling operation of the magnet moving system and the patient support table 60 so that in the second room 41 the magnet 10 and its bore 11 is moved into a position surrounding the patient support table 60 with the part of the second patient on the patient support table 60 at the imaging icocenter location.

In the second room the imaging control computer system 30 is operated to effect imaging of a second patient of the plurality of patients using the magnetic resonance imaging system with the second patient located on the patient support table 60.

In the first room 40 there is provided the first docking station 53 for physical and control connection to the cooperating coupling component 54 on the diagnostic table 50 when the diagnostic table is in communication with the magnet. There is also provided a second coupling component 53A for physical and control connection to the cooperating coupling component 54*t* on the diagnostic table when the diagnostic table is separated from the magnet. Thus the diagnostic table is not merely left standing but it connected to the additional docking station when it is not in use. The imaging control computer 30 communicates with the additional docking station 53A and the original docking station 53 symmetrically and in parallel.

Thus the diagnostic table 50 being connected to the imaging control computer system 30 via the docking station 53A, when imaging is taking place in the second room, acts to provide some of the required sensor values and actuator states to emulate the diagnostic table when used in imaging.

Thus the imaging control computer is convinced into operating with the table 60 by receiving some of its required data and signals from the diagnostic table which is not in use. At the same time the diagnostic table is driven to simulate its functions in imaging so that it moves as instructed by the imaging control computer 30.

However all the required signals and functions cannot be provided in this way and therefore there is provided an emulating computer system 71 which is designed to provide the additional signals and feedback required to provide all of the data necessary to operate the imaging system while disconnected from the diagnostic table and attached instead to the patient support table. For this reason the emulating computer system 71 is connected to the docking station 53A.

Thus signals are generated from the emulating computer system 71 which cooperate with the imaging control computer system 30 by emulating outputs from the disconnected diagnostic table for controlling operation of the imaging system.

In most cases the emulating computer system 71 is a subcomponent of the movement control computer system 70.

The emulating computer system establishes and maintains communication to the imaging control computer system using a defined protocol of the imaging control computer system.

The emulating computer system 71 provides to the imaging control computer system 30 required sensor values and actuator states to emulate the diagnostic table.

The docking station 53 carried on the magnet is also connected to a second coupling 54A carried on the table 60. In this way the parallel instructions and data communicated to the docking station 53 are communicated to the table 60 though the coupling 54A.

The emulating computer system 71 also communicates with the coupling 54A and the movement control computer 70 so as translate the instructions from the imaging control computer system 30 to the table 60 so that the table 60 carries out the required movements and operation expected by the imaging control computer system 30 and normally carried out by the diagnostic table 50.

The movement control computer system includes a control protocol arranged to prevent the magnet from moving if the system detects that the first coupling component is connected to the cooperating coupling component on the diagnostic table.

The movement control computer system includes a control protocol arranged to prevent the magnet from moving beyond a certain range if the system detects that the RF probe 15 is still connected to RF receptacles on the magnet.

The emulating computer system 70 provides a look-up-table 72 to map physical values to virtual values for communication to the imaging control computer system to enable safe and effective imaging. That is the emulating computer system supplies a virtual value for the position of one or more system parameters which are sufficient for the imaging control computer system to compute and control imaging and safety aspects of the system.

In particular, the emulating computer system 70 supplies a virtual value for the position of the patient table position which is sufficient for the imaging control computer system to compute and control specific-absorption rate (SAR).

Table 1 provides a simplieified version of the Look Up Table for explanation purposes.

The following provides an example of the LUT application.

1. Patient registration: data entered by a registration system 80 into both the image control computer 30 and the movement control computer 70 systems.

2. The patient is setup on operating room table 60.

3. The image control computer system 30 computes SAR patient body model etc.

4. On the image control computer system 30 the imaging sequence selected and parameters are set.

5. Normally the diagnostic table 50 is moved to iso-center. However, in the operating room 41, it is the magnet that is moved.

The preferred implementation has the user only interact with the movement control computer 70 and the table emulator 71 interacts directly with the image control computer system 30 to provide a correct value for the image control computer system 30, bypassing the diagnostic table 50 entirely.

In a second implementation, the table emulator 71 provides an input to the diagnostic table 50 to set it to the desired position.

In a third implementation, the user is prompted to use the image control computer system 30 to position the diagnostic table 50 appropriately.

6. For example, during patient setup and imaging, the following positions are equivalent:
 a) "Magnet at PSCP in OR, −30 mm over tabletop"="diagnostic table at front of bore in DR, 0 mm in bore"
 b) "Magnet 9070 mm over OR tabletop"="diagnostic table at front of bore in DR, 1000 mm in bore"

image the heart (rather the scanner is moved further over the table), the system would normally apply an incorrect setting.

That is, both the emulating computer system and the imaging control computer system computer has information on patient height/weight, age, position on the table, orientation to the magnet and wherein the emulating computer system has a look up table (LUT) to convert magnet position along the patient support table to a value that the imaging control computer system expects to compute and control specific-absorption rate (SAR).

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

TABLE 1

SIMPLIFIED LOOKUP TABLE - SAMPLE ENTRY

| IMRIS System State | Siemens System State | Position adjustment for Diagnostic tabletop in bore [PTAB position] |
|---|---|---|
| Operating table = ORT300 Tabletop = neuro Magnet position over table = PSCP + 25 mm IMRIS also knows patient info | patient Age = 23 Height = 1800 mm +/− 5 mm Weight = 75 kg +/− 0.5 kg Orientation = head first (or feet first) Patient position = supine (or prone) system bore air temperature = 23 Celcius diagnostic patient table position (PTAB) = 1000 mm imaging TX Coil = volume (or local) Anatomy = head (or heart or liver) MR Console = normal level (or first or second) MR sequence = turbo spin scho (TSE) (or SE, . . . ) Other MR sequence specific parameters: Flip angle = X, . . . SAR patient body model values Head cylinder mass = . . . Head cylinder length = . . . Head cylinder radius = . . . | PTAB change required for desired SAR limit = +100 mm |

7. The above calculation would differ for each table top since:
 a) PSCP depends on the tabletop
 b) Each tabletop has a different length.

The key benefit is when imaging in multiple locations with the same patient in a single imaging session (ie without re-registering the patient) where the imaged locations differ in their SAR values.

For example, imaging a patient for neuro-imaging, then moving the MRI scanner further over the table to image the heart.

Since the head and heart have different SAR limits, the image control computer system 30 needs to be informed that a new SAR limit should be used. Since in the preferred configuration, the diagnostic table does not need to be moved to

The invention claimed is:

1. A method for imaging a part of each of a plurality of patients comprising:
 providing a plurality of rooms each arranged for use in imaging a patient from said plurality of patients independently, the plurality of the rooms including at least a first room for a diagnostic procedure and a second room for an interventional procedure;
 providing a magnetic resonance imaging system for obtaining images of a part of a patient of the plurality of patients, the magnetic resonance imaging system comprising:
 a magnet having a cylindrical bore with a horizontal axis of the bore longitudinal of the magnet;
 a field control arrangement for controlling and varying magnetic fields of the magnet, a radio frequency transmission and detection system for eliciting and detecting NMR signals from the part in response to the magnetic fields, an RF probe arranged to be located adjacent to the part at an imaging location in the bore, a display monitor for displaying the detected signals;

a diagnostic table arranged to be mounted at a first end of the bore for movement relative to the magnet longitudinally of the bore toward a second end of the bore for carrying the part of the patient into an imaging location in the bore, the diagnostic table being separable from the magnet so as to disconnected therefrom;

and an imaging control computer system for controlling operation of the magnetic resonance imaging system including the field control arrangement, the detection system, the RF probe, the display monitor and the diagnostic table;

in the first room using the imaging control computer system to effect imaging of a first patient of the plurality of patients using the magnetic resonance imaging system with the first patient located on the diagnostic table, the imaging control computer system being connected during the imaging with the diagnostic table by a coupling on the diagnostic table which connects to a docking station on the magnet for communicating of imaging control signals to and from the diagnostic table;

providing a magnet moving system for moving the magnet from the first room to the second room;

providing a patient support table mounted in the second room arranged for the interventional procedure on a second patient from said plurality of patients;

the patient support table being operable for movement of a patient support portion to different positions of the patient relative to the magnet;

the patient support table being arranged for cooperation with associated elements arranged for use in the interventional procedure;

providing a movement control computer system for controlling operation of the magnet moving system and the patient support table;

moving the magnet from the first room to the second room by;

disconnecting the coupling on the diagnostic table from the docking station of the magnet so that the diagnostic table remains with the first room; and operating the movement control computer system to control operation of the magnet moving system and the patient support table;

so that in the second room the magnet and its bore is moved into a position surrounding the patient support table with the part of the second patient on the patient support table at the imaging location;

in the second room using the control computer system to effect imaging of a second patient of the plurality of patients using the magnetic resonance imaging system with the second patient located on the patient support table, the imaging control computer system being connected during the imaging with the patient support table by a coupling on the patient support table which connects to the docking station on the magnet for communicating of imaging control signals to and from the patient support table;

the imaging control computer system being connected during the imaging in the second room with the diagnostic table by said coupling on the diagnostic table which connects to a second docking station in the first room for communicating of imaging control signals to and from the diagnostic table;

and providing an emulating computer system separate from the imaging control computer system which communicates with the imaging control computer system by generating signals emulating outputs from the disconnected diagnostic table for controlling operation of the imaging system.

2. The method according to claim 1 wherein the emulating computer system is a sub-component of the movement control computer system.

3. The method according to claim 1 wherein the emulating computer system establishes and maintains communication to the imaging control computer system using a defined protocol.

4. The method according to claim 1 wherein the emulating computer system provides said emulating outputs to the imaging control computer system by generating required emulated sensor values and emulated actuator states of said disconnected diagnostic table.

5. The method according to claim 1 wherein the movement control computer system prevents the magnet from moving if the system detects that the docking station of the magnet is connected to the cooperating coupling component on the diagnostic table.

6. The method according to claim 1 wherein the docking station of the magnet and the cooperating coupling component provide connection of power, sense lines and optical fibers to enable communication between the diagnostic table and the magnet.

7. The method according to claim 1 wherein the movement control computer system prevents the magnet from moving beyond a certain range if the system detects that the RF probe is still connected to RF receptacles on the magnet.

8. The method according to claim 1 wherein the emulating computer system provides a look-up-table to map physical values to virtual values for communication to the imaging control computer system to enable safe and effective imaging.

9. The method according to claim 1 wherein the emulating computer system supplies a virtual value for the position of one or more system parameters which are sufficient for the imaging control computer system to compute and control imaging and safety aspects of the system.

10. The method according to claim 1 wherein the emulating computer system supplies a virtual value for the position of the patient table position which is sufficient for the imaging control computer system to compute and control specific-absorption rate (SAR).

11. The method according to claim 10 wherein both the emulating computer system and the imaging control computer system computer has information on patient height/weight, age, position on the table, orientation to the magnet and wherein the emulating computer system has a look up table (LUT) to convert magnet position along the patient support table to a value that the imaging control computer system expects to compute and control specific-absorption rate (SAR).

* * * * *